United States Patent
Hara et al.

(10) Patent No.: US 11,619,500 B2
(45) Date of Patent: Apr. 4, 2023

(54) INFORMATION PROCESSING APPARATUS, INFORMATION PROCESSING SYSTEM, STORAGE MEDIUM, AND INFORMATION PROCESSING METHOD

(71) Applicant: TOYOTA JIDOSHA KABUSHIKI KAISHA, Toyota (JP)

(72) Inventors: Yusuke Hara, Musashino (JP); Shuhei Aketa, Koto-ku (JP); Toru Yanagida, Nagoya (JP); Shin Sakurada, Toyota (JP); Tae Sugimura, Miyoshi (JP); Yasutaka Ujihara, Meguro-ku (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 321 days.

(21) Appl. No.: 16/936,024

(22) Filed: Jul. 22, 2020

(65) Prior Publication Data
US 2021/0024103 A1    Jan. 28, 2021

(30) Foreign Application Priority Data
Jul. 22, 2019  (JP) .............................. JP2019-134648

(51) Int. Cl.
*G01C 21/34* (2006.01)
*G16H 40/20* (2018.01)
(Continued)

(52) U.S. Cl.
CPC ....... *G01C 21/3407* (2013.01); *G06F 16/248* (2019.01); *G06Q 50/30* (2013.01); *G16H 40/20* (2018.01)

(58) Field of Classification Search
CPC combination set(s) only.
See application file for complete search history.

(56) References Cited

U.S. PATENT DOCUMENTS 10,580,306 B1 *  3/2020  Harris ................. H04W 4/40
2018/0053423 A1 *  2/2018  DaCosta ........ G06Q 10/063114
(Continued)

FOREIGN PATENT DOCUMENTS

JP    2012-103886 A    5/2012
JP    2015-118489 A    6/2015
(Continued)

*Primary Examiner* — Anne Marie Antonucci
*Assistant Examiner* — Amelia Vorce
(74) *Attorney, Agent, or Firm* — Oliff PLC

(57) ABSTRACT

An information processing apparatus includes a controller. The controller accumulates a scheduled vacant time period of a medical service, the scheduled period being received from an information management apparatus, in association with a medical facility corresponding to the information management apparatus. When a medical service request is received from a terminal apparatus, the controller searches for a particular medical facility as an available medical facility, being capable of providing a medical service corresponding to a medical service item in the scheduled vacant time period and that can be reached from the location of the terminal apparatus included in the medical service request in the scheduled vacant time period. The controller sends a notification of the available medical facility to the terminal apparatus sending the medical service request. The controller sends a consultation request to receive the medical service to the information management apparatus corresponding to the available medical facility.

20 Claims, 13 Drawing Sheets

(51) Int. Cl.
*G06F 16/248* (2019.01)
*G06Q 50/30* (2012.01)

(56) References Cited

U.S. PATENT DOCUMENTS

| | | | |
|---|---|---|---|
| 2018/0218338 A1* | 8/2018 | Hengerer | G06F 16/24575 |
| 2019/0035501 A1* | 1/2019 | Zhang | G16H 80/00 |
| 2019/0099118 A1* | 4/2019 | Patel | A61B 5/6893 |
| 2019/0277643 A1* | 9/2019 | Szubbocsev | G01C 21/3679 |
| 2019/0359220 A1* | 11/2019 | Wilson | G05D 1/0055 |
| 2019/0361437 A1* | 11/2019 | Wilson | G06F 40/58 |
| 2021/0024103 A1* | 1/2021 | Hara | G01C 21/3407 |
| 2021/0041868 A1* | 2/2021 | Fields | G06Q 30/0207 |
| 2021/0056483 A1 | 2/2021 | Kajiwara et al. | |
| 2022/0073110 A1* | 3/2022 | Kleve | G08B 1/08 |

FOREIGN PATENT DOCUMENTS

| | | |
|---|---|---|
| JP | 2018-073107 A | 5/2018 |
| WO | 2019/130056 A1 | 7/2019 |

\* cited by examiner

INFORMATION PROCESSING APPARATUS, INFORMATION PROCESSING SYSTEM, STORAGE MEDIUM, AND INFORMATION PROCESSING METHOD

CROSS-REFERENCE TO RELATED APPLICATION

The present application claims priority to Japanese Patent Application No. 2019-134648 filed on Jul. 22, 2019, the entire disclosure of which is incorporated herein by reference.

TECHNICAL FIELD

The present disclosure relates to an information processing apparatus, an information processing system, a storage medium, and an information processing method.

BACKGROUND

It is desired to reduce the costs associated with medical services. A transportation system for transporting patients to and from medical facilities has been developed, in which a medical interview is conducted before a patient arrives at a medical facility and information obtained in the medical interview is sent to the medical facility. As a result, the time for providing medical services is reduced (refer to PTL 1).

CITATION LIST

Patent Literature

PTL 1: JP 2018-073107 A

SUMMARY

In the medical field, it is desired to reduce not only the costs of medical service providers but also patient waiting times. However, the system disclosed in PTL 1 does not reduce waiting times.

An object of the present disclosure having been made in consideration of the circumstances described above is to reduce the waiting times for patients who desire to receive services at medical facilities.

An information processing apparatus according to an embodiment of the present disclosure includes a controller. The controller accumulates a scheduled vacant time period of a medical service, the scheduled vacant time period being received from an information management apparatus, in association with a medical facility corresponding to the information management apparatus. When a medical service request including a desired medical service item and a location of a terminal apparatus is received from a terminal apparatus, the controller searches a memory for a particular medical facility as an available medical facility, the particular medical facility being capable of providing a medical service corresponding to the medical service item in the scheduled vacant time period and that can be reached from the location of the terminal apparatus included in the medical service request in the scheduled vacant time period. The controller sends a notification of the available medical facility to the terminal apparatus sending the medical service request. The controller sends a consultation request to receive the medical service to the information management apparatus corresponding to the available medical facility.

An information processing system according to an embodiment of the present disclosure includes an information processing apparatus, a terminal apparatus, and an information management apparatus. The information processing apparatus includes a controller. The controller accumulates a scheduled vacant time period of a medical service, the scheduled vacant time period being sent from the information management apparatus, in association with a medical facility corresponding to the information management apparatus. When a medical service request including a desired medical service item and a location of a terminal apparatus is sent from the terminal apparatus, the controller searches a memory for a particular medical facility as an available medical facility, the particular medical facility being capable of providing a medical service corresponding to the medical service item in the scheduled vacant time period and that can be reached from the location of the terminal apparatus included in the medical service request in the scheduled vacant time period. The controller sends a notification of the available medical facility to the terminal apparatus sending the medical service request. The controller sends a consultation request to receive the medical service to the information management apparatus corresponding to the available medical facility.

A non-transitory computer-readable storage medium according to an embodiment of the present disclosure stores a program which, when executed by an information processing apparatus, causes the information processing apparatus to execute a process. The process includes receiving a scheduled vacant time period of a medical service from an information management apparatus, accumulating the scheduled vacant time period in association with a medical facility corresponding to the information management apparatus sending the scheduled vacant time period, receiving from a terminal apparatus a medical service request including a desired medical service item and a location of the terminal apparatus, searching for a particular medical facility as an available medical facility in accordance with the scheduled vacant time period accumulated in association with the medical facility, the particular medical facility being capable of providing a medical service corresponding to the medical service item included in the medical service request in the scheduled vacant time period and that can be reached from the location of the terminal apparatus included in the medical service request in the scheduled vacant time period, sending a notification of the available medical facility to the terminal apparatus sending the medical service request, and sending a consultation request to receive the medical service to the information management apparatus corresponding to the available medical facility.

An information processing method implemented by an information processing apparatus according to an embodiment of the present disclosure includes receiving a scheduled vacant time period of a medical service from an information management apparatus, accumulating the scheduled vacant time period in association with a medical facility corresponding to the information management apparatus sending the scheduled vacant time period, receiving from a terminal apparatus a medical service request including a desired medical service item and a location of the terminal apparatus, searching for a particular medical facility as an available medical facility in accordance with the scheduled vacant time period accumulated in association with the medical facility, the particular medical facility being capable of providing a medical service corresponding to the medical service item included in the medical service request in the scheduled vacant time period and that can be reached from the location of the terminal apparatus included in the medical service request in the scheduled vacant time period, sending a notification of the available medical facility to the terminal apparatus sending the medical service request, and sending a consultation request to receive the medical service to the information management apparatus corresponding to the available medical facility.

The information processing apparatus, the information processing system, the storage medium, and the information processing method according to an embodiment of the present disclosure can reduce patient waiting times.

DETAILED DESCRIPTION

Hereinafter, an embodiment of the present disclosure is described with reference to the drawings.

Figure 1:
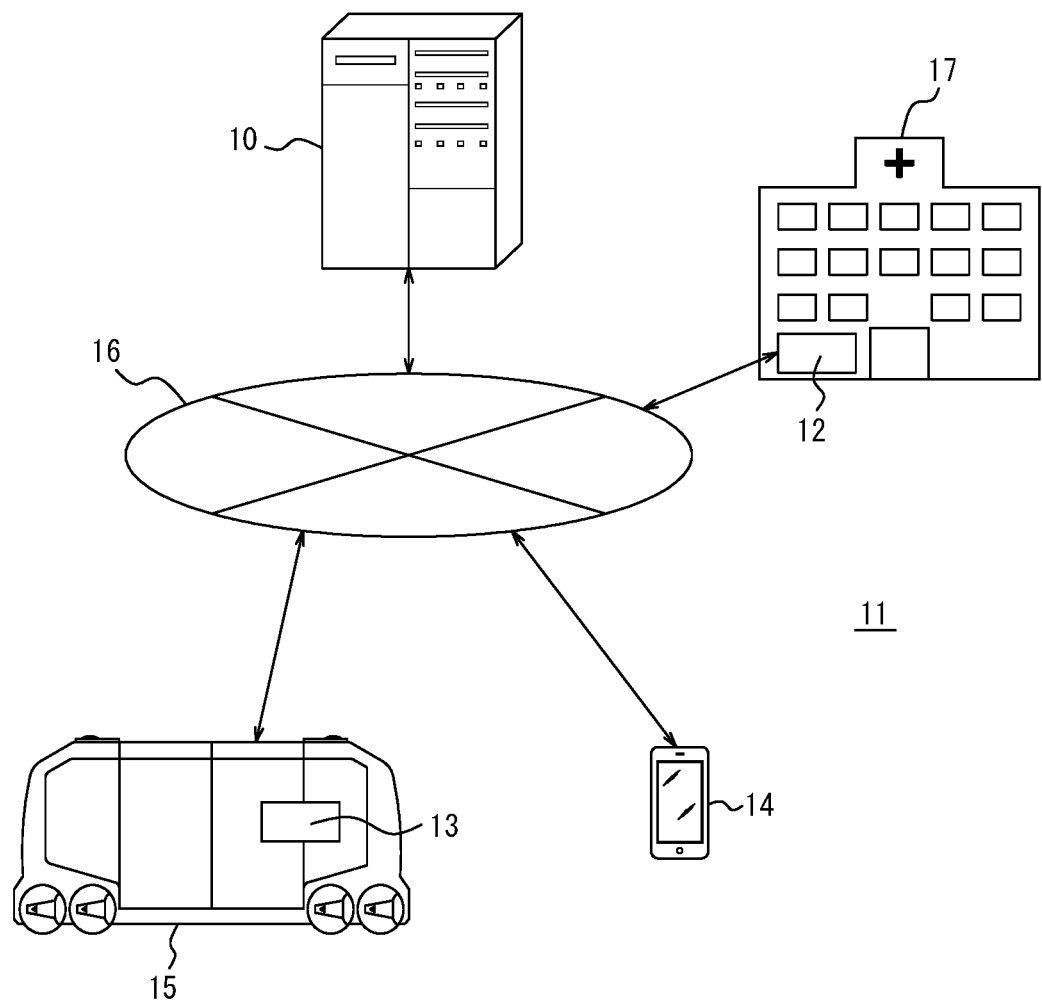
FIG. 1 is a configuration diagram illustrating an overall configuration of an information processing system including an information processing apparatus according to an embodiment of the present disclosure.

An information processing system 11 including an information processing apparatus 10 according to an embodiment of the present disclosure is described in outline with reference to FIG. 1. The information processing system 11 includes an information management apparatus 12, a first terminal apparatus 13, a second terminal apparatus 14, and the information processing apparatus 10.

The information management apparatus 12 includes one server apparatus or a plurality of server apparatuses that are capable of communicating with each other. The first terminal apparatus 13 is an electronic device specific to the information processing system 11 but may be, for example, a generic electronic device such as a personal computer (PC). The first terminal apparatus 13 is installed in a vehicle 15. The second terminal apparatus 14 is, for example, a generic electronic device such as a smartphone or a PC, but the second terminal apparatus 14 is not limited to this example and may be an electronic device specific to the information processing system 11. The second terminal apparatus 14 is a device expected to be carried by a person. The information processing apparatus 10 includes one server apparatus or a plurality of server apparatuses that are capable of communicating with each other. While FIG. 1 illustrates one information management apparatus 12, one first terminal apparatus 13, and one second terminal apparatus 14 for ease of description, the information processing system 11 may include at least one information management apparatus 12, at least one first terminal apparatus 13, and at least one second terminal apparatus 14.

The information management apparatus 12, the first terminal apparatus 13, the second terminal apparatus 14, and the information processing apparatus 10 are communicably connected to a network 16 which, for example, includes a mobile communication network and the Internet. At least part of the information processing system 11 is used for providing a mobility service (MaaS: Mobility-as-a-Service). Service providers can provide mobility services such as a ridesharing service, a mobile hotel, and a mobile retail shop using the first terminal apparatus 13 and the vehicle 15.

The outline of the information processing system 11 according to the present embodiment is hereinafter further explained. The information management apparatus 12 is installed in an individual medical facility 17 and, for example, appointments for medical services on future dates are input to the information management apparatus 12. In accordance with the appointments for medical services, the information management apparatus 12 generates a scheduled vacant time period at which provision of a medical service is available. It should be noted that, as used herein, "generate" denotes generating information on a target such as a scheduled vacant time period. The information management apparatus 12 sends the scheduled vacant time period to the information processing apparatus 10. It should be noted that, as used herein, "send" denotes sending information on a target such as a scheduled vacant time period. The information processing apparatus 10 stores the scheduled vacant time period in association with the medical facility 17. A person who desires to receive a medical service inputs a desired medical service item into a terminal apparatus such as the first terminal apparatus 13 or the second terminal apparatus 14. When the terminal apparatus detects input of a desired medical service item, the terminal apparatus sends to the information processing apparatus 10 a medical service request including a location of the terminal apparatus and the medical service item. The information processing apparatus 10 searches for, as an available medical facility that can provide a medical service, a particular medical facility 17 at which a medical service corresponding to the medical service item can be provided in a scheduled vacant time period and that can be reached in the scheduled vacant time period from the location of the terminal apparatus. The information processing apparatus 10 notifies the terminal apparatus of the available medical facility. It should be noted that, as used herein, "notify" denotes sending information on a target such as an available medical facility. The information processing apparatus 10 sends a consultation request to the information management apparatus 12 of the medical facility 17 that is determined as an available medical facility.

As described above, in the present embodiment, the information processing apparatus 10 can accumulate scheduled vacant time periods that are scheduled in advance at individual medical facilities 17. It should be noted that, as used herein, "accumulate" denotes accumulating information on a target such as a scheduled vacant time period. When the information processing apparatus 10 that accumulates the schedule of vacant times for many medical facilities 17 receives a medical service request from a terminal apparatus, a particular medical facility 17 that can provide a medical service in a scheduled vacant time period is notified to the terminal apparatus and a consultation request is notified to the particular medical facility 17. It should be noted that, as used herein, "receive" denotes receiving information on a target such as a medical service request. As a result, a person who desires to receive a medical service and inputs a medical service item to a terminal apparatus can be guided to the medical facility 17 at which the waiting time would be relatively short. Thus, in comparison to conventional techniques, it is possible to reduce the waiting time for people who desire to receive medical services.

Next, the constituents of the information processing system 11 are described in detail.

Figure 2:
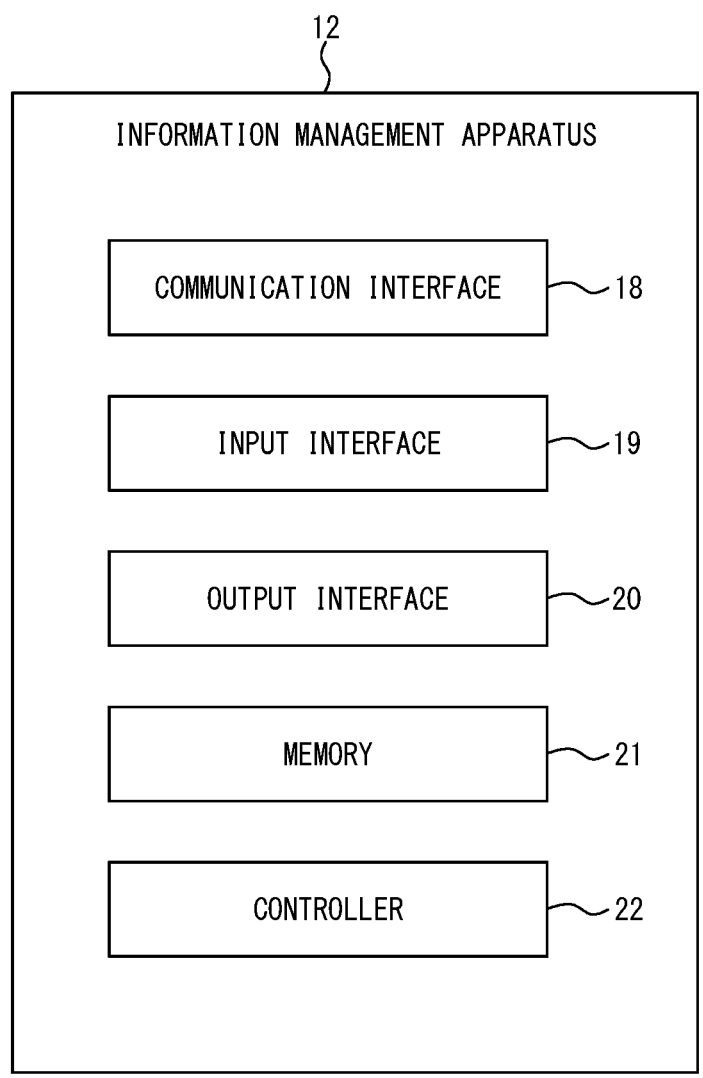
FIG. 2 is a functional block diagram schematically illustrating a configuration of the information management apparatus in FIG. 1.

As illustrated in FIG. 2, the information management apparatus 12 includes a communication interface 18, an input interface 19, an output interface 20, a memory 21, and a controller 22.

The communication interface 18 includes a communication module that establishes communication via a dedicated line. The communication interface 18 also includes a communication module that establishes connection with the network 16. For example, the communication interface may include a communication module compliant with mobile communication standards such as the fourth generation (4G) and the fifth generation (5G) standards. In the present embodiment, the information management apparatus 12 is connected to the network 16 via the communication interface 18. The communication interface 18 sends and receives various kinds of information via the network 16.

The input interface 19 includes at least one interface that detects user inputs. For example, the input interface 19 may be, but is not limited to, physical keys, capacitive keys, a touch screen provided in combination with a display of the output interface 20, or a microphone that accepts voice input.

The output interface 20 includes at least one interface that outputs information to notify users. For example, the output interface 20 may be, but is not limited to, a display that outputs information as images or a speaker that outputs information as sound.

The memory 21 may be, but is not limited to, a semiconductor memory, a magnetic memory, an optical memory, or the like. The memory 21 may function as, for example, a primary storage unit, an auxiliary storage unit, or a cache memory. The memory 21 stores any information that is used for operation of the information management apparatus 12. The memory 21 may store, for example, a system program and an application program. The memory 21 may store a medical service schedule and identification information for the information management apparatus 12. The medical service schedule is, for example, a plan of medical services provided at the medical facility 17. The identification information on the information management apparatus 12 is information that can be used to uniquely identify the information management apparatus 12 in the information processing system 11. The information stored in the memory 21 may be updated using, for example, information received from the network 16 via the communication interface 18.

The controller 22 includes at least one processor. In the present embodiment, a "processor" may be, but is not limited to, a general processor or a processor specific to a particular processing operation. The controller 22 controls the entire operation of the information management apparatus 12.

When the input interface 19 detects a user input for requesting registration of the medical facility 17 with the information processing apparatus 10, the controller 22 generates a registration request. The controller 22 includes an identification number of the information management apparatus 12, clinical departments, medical service items which can be provided, and a facility location of the medical facility 17 in the registration request which is generated. The controller 22 sends the generated registration request to the information processing apparatus 10 via the communication interface 18.

The controller 22 manages a medical service schedule in the medical facility 17.

The controller 22 recognizes an appointment registration request in accordance with, for example, a user input detected by the input interface 19. When the controller 22 recognizes an appointment registration request, the controller 22 causes the output interface 20 to output information requesting a user input indicating the clinical department for which the user desires to arrange an appointment. When a user input indicating a clinical department for the appointment is detected, the controller 22 causes the output interface 20 to output available time slots in a medical service schedule stored in the memory 21.

The available time slots are time slots that are within the medical service hours of the medical facility 17 and from which at least scheduled time slots with appointments are excluded. The medical service hours of the medical facility 17 are predetermined hours during which the medical facility 17 provides medical services to patients, such as the periods between 9 am and 1 pm, and 3 pm and 6 pm. The available time slots may be time slots excluding fixed time slots. A fixed time slot is a time slot for which priority is given to a consultation request submitted by a terminal apparatus, such as a time slot of every hour for fifteen minutes from a quarter to the hour, or a time slot for one hour before the end of the medical service hours. The fixed time slot can be set for each medical facility 17.

When the input interface 19 detects a user input indicating a designated time in the available time slots, the controller 22 updates the medical service schedule to include the designated time in the scheduled time slots. The controller 22 registers the appointment by updating the medical service schedule. The length of a designated time can be an average time length determined in accordance with a past average time for the medical services of each clinical department in the medical facility 17 or a past average time for each doctor, or determined by machine learning. The controller 22 stores the updated medical service schedule in the memory 21.

The controller 22 sends, together with identification information for the information management apparatus 12, at least the scheduled vacant time periods in the medical service schedule stored in the memory 21 to the information processing apparatus 10 via the communication interface 18. The scheduled vacant time periods are time slots obtained by excluding scheduled time slots from the medical service schedule. A scheduled vacant time period is, for example, a time that, before a consultation request submitted by a terminal apparatus is reflected in the medical service schedule, is not determined as a fixed time slot and that is not targeted for any medical service appointment.

The scheduled vacant time periods may include not only the scheduled vacant time periods per se but also information from which a scheduled vacant time period can be determined, such as an entire medical service schedule. The controller 22 may send the scheduled vacant time periods under a predetermined condition. For example, the controller 22 may send the scheduled vacant time periods periodically, regularly, or in response to a trigger such as an update to the medical service schedule. When the medical service schedule is updated in response to reception of a consultation request as described below, the controller 22 may send the medical service schedule to the information processing apparatus 10 using the update as the condition.

When a consultation request for a medical service in a scheduled vacant time period is received from the information processing apparatus 10, the controller 22 updates the medical service schedule to include, in the scheduled time slots, the time included in the consultation request for which the consultation is requested, as described later. The controller 22 stores the updated medical service schedule in the memory 21.

Based on a user input during medical service hours, the controller 22 updates the medical service schedule for the current day. For example, when a user input indicating that a patient with an appointment has arrived at a corresponding medical facility by a scheduled time slot is detected, the controller 22 causes the output interface 20 to output information for ordering a consultation with the patient of the appointment in the time slot. For example, when a user input indicating completion of a medical service is detected, the controller 22 updates subsequent time slots with appointments and scheduled vacant time periods and stores in the memory 21 the subsequent time slots with appointments and the scheduled vacant time periods. For example, when a user input indicating that a patient with an appointment has arrived at a corresponding medical facility after a scheduled time slot or a user input indicating that a patient without an appointment attends a corresponding medical facility is detected, the controller 22 causes the output interface 20 to output information for ordering a consultation with the patient in a scheduled vacant time period after the current time.

The first terminal apparatus 13 is installed in the vehicle 15 as described above. For example, the vehicle 15 may be an autonomous vehicle that can perform automated driving or vehicle-following, but is not limited to this and may be any vehicle in which the first terminal apparatus 13 can be installed.

In outline, the first terminal apparatus 13 automatically generates control information using automatic driving control software and sends the control information to the vehicle 15. The vehicle 15 performs vehicle control in accordance with the received control information. For example, the vehicle control may be, but is not limited to, automated driving control. At least part of an application programming interface (API) which defines specifications of control information is disclosed to service providers. Service providers can freely develop the automatic driving control software for the first terminal apparatus 13 by programming with the use of the disclosed API. Thus, the service providers can provide any mobility service by installing equipment according to a particular purpose in the cabin space of the vehicle 15 and developing automatic driving control software by programming with the use of an API according to the purpose.

Figure 3:
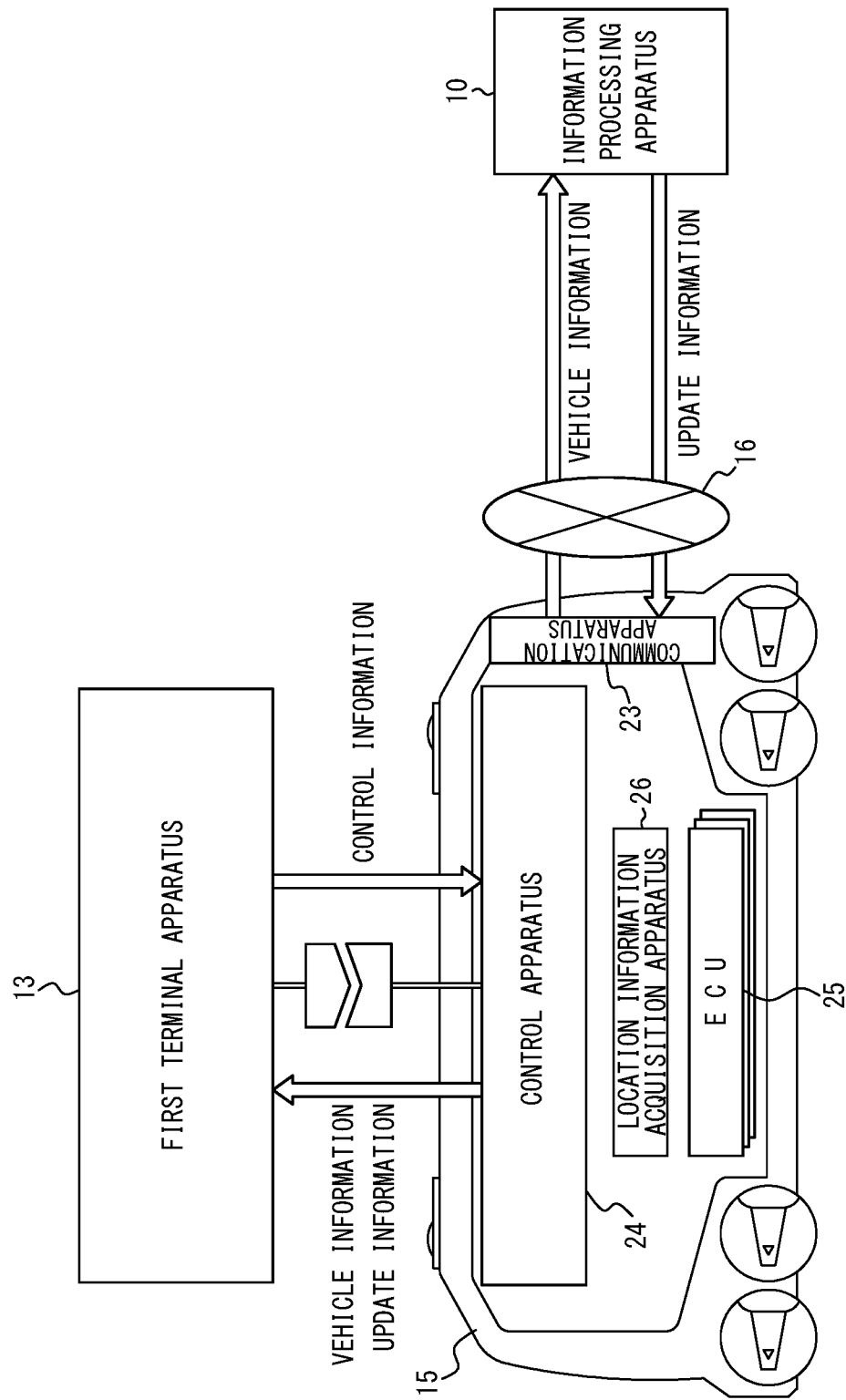
FIG. 3 is a functional block diagram schematically illustrating a configuration of a vehicle in FIG. 1.

As illustrated in FIG. 3, the vehicle 15 includes a communication apparatus 23, a control apparatus 24, a plurality of electronic control units (ECUs) 25, a location information acquisition apparatus 26, and the first terminal apparatus 13. The communication apparatus 23, the control apparatus 24, the ECUs 25, the location information acquisition apparatus 26, and the first terminal apparatus 13 are communicably connected to each other via, for example, an in-vehicle network such as a controller area network (CAN) or dedicated lines.

The communication apparatus 23 may be a dedicated on-board communication device. To connect to the network 16, the communication apparatus 23 may include a communication module compliant with mobile communication standards such as the 4G and 5G standards.

The control apparatus 24 performs vehicle control in accordance with control information received from the first terminal apparatus 13. For example, the vehicle control is, but not limited to, automated driving control for reaching a destination. The automated driving includes, for example, Levels 1 to 5 as defined by the Society of Automotive Engineers (SAE), but the automated driving is not limited to this example and may be defined in any form. The vehicle control is performed by the control apparatus 24 and the ECUs 25 cooperating with each other. The control apparatus 24 includes a communication module that communicates with the first terminal apparatus 13, the communication apparatus 23, and the ECUs 25, one or more memories that store a system program, an application program, and the like, and a controller including one or more processors that control an operation of the entire control apparatus 24.

The control apparatus 24 receives, for example, various kinds of vehicle information (for example, speed, location, and automated driving state) regarding the vehicle 15 from the ECUs 25 or the like. The control apparatus 24 sends the vehicle information to the first terminal apparatus 13 and also to the information processing apparatus 10 using the communication apparatus 23. The control apparatus 24 also receives update information for the system program of the first terminal apparatus 13 from the information processing apparatus 10 via the communication apparatus 23 and sends the update information to the first terminal apparatus 13. When control information is received from the first terminal apparatus 13, the control apparatus 24 performs vehicle control for the vehicle 15 in accordance with the control information.

The ECUs 25 control operations of the vehicle 15 in cooperation with the control apparatus 24. Specifically, the ECUs 25 receive from the control apparatus 24 control instructions based on control information and control operation of the vehicle 15 in accordance with the control instructions. For example, the ECUs 25 control the operating variables of the vehicle 15 to reach values indicated by control instructions. The ECUs 25 collect measured values regarding the control or operating variables of the vehicle 15 from various sensors installed in the vehicle 15 at each control timing and send the measured values to the control apparatus 24.

The location information acquisition apparatus 26 includes at least one receiver for a satellite navigation system. For example, the location information acquisition apparatus 26 may include a global positioning system (GPS) receiver. The location information acquisition apparatus 26 obtains a measured value corresponding to the location of the vehicle 15 as location information and sends the measured value to the control apparatus 24.

Figure 4:
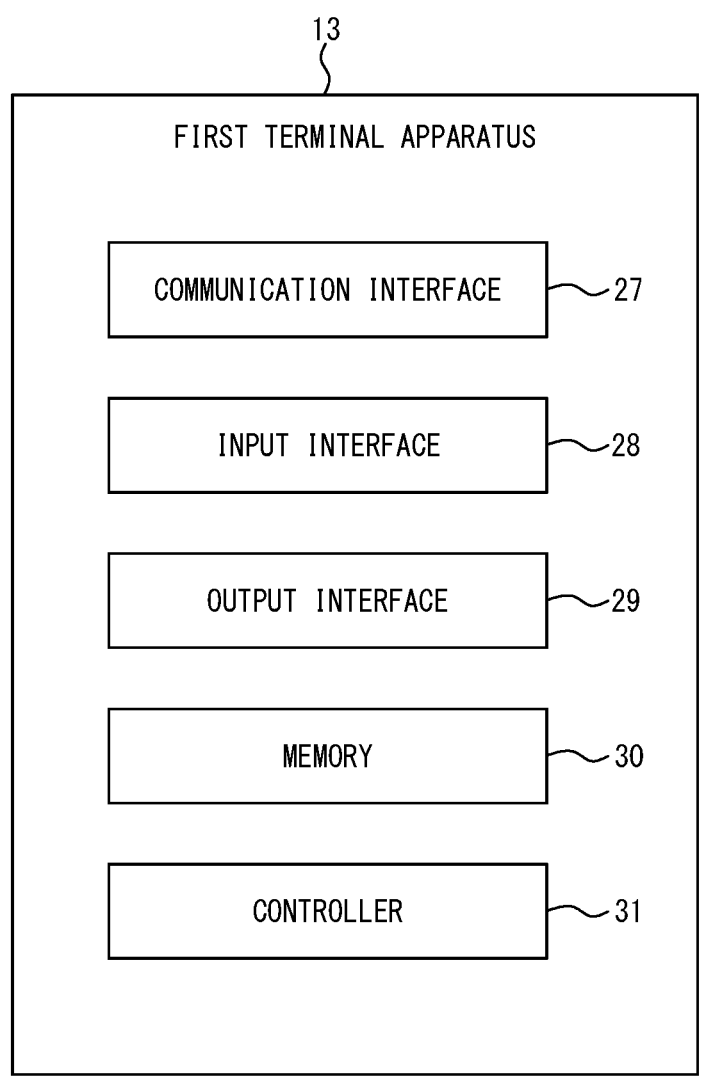
FIG. 4 is a functional block diagram schematically illustrating a configuration of a first terminal apparatus in FIG. 1.

As illustrated in FIG. 4, the first terminal apparatus 13 includes a communication interface 27, an input interface 28, an output interface 29, a memory 30, and a controller 31.

The communication interface 27 includes a communication module that communicates with the communication apparatus 23, the control apparatus 24, and the location information acquisition apparatus 26. In the present embodiment, the first terminal apparatus 13 is connected to the network 16 via the communication interface 27 and the communication apparatus 23. The communication interface 27 may include a communication module compliant with mobile communication standards such as 4G and 5G and may be connected directly to the network 16. The communication interface 27 sends and receives various kinds of information via at least the network 16.

The input interface 28 includes at least one interface that detects user inputs. For example, the input interface 28 may be, but is not limited to, physical keys, capacitive keys, a touch screen provided in combination with a display of the output interface 29, or a microphone that accepts voice input.

The output interface 29 includes at least one interface that outputs information to notify users. For example, the output interface 29 may be, but not limited to, a display that outputs information as images or a speaker that outputs information as sound.

The memory 30 is, but not limited to, a semiconductor memory, a magnetic memory, an optical memory, or the like. The memory 30 may function as, for example, a primary storage unit, an auxiliary storage unit, or a cache memory. The memory 30 stores any information that is used for an operation of the first terminal apparatus 13. The memory 30 may store, for example, a system program and an application program. The memory 30 may store identification information for the first terminal apparatus 13. The identification information for the first terminal apparatus 13 is information that can be used to uniquely identify the first terminal apparatus 13 in the information processing system 11. The memory 30 may store the time required for treatment corresponding to each of the specified medical service items described later. The information stored in the memory 30 may be updated using, for example, information received from the network 16 via the communication interface 27.

The controller 31 includes at least one processor. In the present embodiment, a "processor" may be, but is not limited to, a general processor or a processor specific to a particular processing operation. The controller 31 controls the entire operation of the first terminal apparatus 13.

When the input interface 28 detects a user input regarding a medical service item, the controller 31 recognizes a desired medical service item in accordance with the information for the detected user input. The medical service item may be recognized from specified medical service items that are determined in advance. For example, medical service items that take relatively short and regular times can be determined as the specified medical service items. Alternatively, an unspecified medical service item can be recognized as a medical service item.

Various methods can be used to recognize desired medical service items. The controller 31 may recognize a desired medical service item, for example, such that the controller 31 causes the output interface 29 to output information which enables a person making the input to recognize the specified medical service items described above in a selectable manner and the controller 31 detects a user input which selects from the specified medical service items. Alternatively, the controller 31 may, for example, cause the output interface 29 to output information on questions about the medical condition of the person making the input and recognize a desired medical service item in accordance with user inputs in answer to the questions.

The controller 31 may estimate a time required to provide a medical service corresponding to the desired medical service item. The controller 31 may estimate the time in accordance with the times required to provide medical services corresponding to individual medical service items that are stored in the memory 30. The times required to provide medical services corresponding to individual medical service items may be, for example, received from the information processing apparatus 10 and stored in the memory 30.

After the controller 31 recognizes a desired medical service item, the controller 31 receives the location of the vehicle 15 from the location information acquisition apparatus 26 via the control apparatus 24. The controller 31 generates a medical service request including the received location of the vehicle 15 and the desired medical service item. The controller 31 may include identification information for the first terminal apparatus 13 in the medical service request. The controller 31 may include identification information the person making the input in the medical service request. The identification information for the person making the input may be the name of the person that is recognized in accordance with a user input or a number that is newly assigned to the person each time a medical service request is created. The controller 31 may include the time required to provide the medical service corresponding to the desired medical service item in the medical service request.

After the controller 31 completes generation of the medical service request, the controller 31 sends the medical service request to the information processing apparatus 10 via the communication interface 27.

When the communication interface 27 receives a notification of an available medical facility, which will be described later, for the medical service request from the information processing apparatus 10, the controller 31 generates control information for moving the vehicle 15 to the available medical facility. When the notification of an available medical facility includes a time for which an appointment is scheduled, the controller 31 may generate control information for moving the vehicle 15 to reach the available medical facility by a start time of the time for which an appointment is scheduled.

In a configuration in which the vehicle 15 is capable of automated driving, the control information may include operating instructions for controlling the vehicle 15 to travel from a current location to an available medical facility along a specified route. In a configuration in which the vehicle 15 is incapable of automated driving, the control information may include, as information for moving the vehicle 15 to the available medical facility, a specified route leading to an available medical facility that is to be communicated to a driver of the vehicle 15. Alternatively, the control information may include only the location of the available medical facility.

The controller 31 sends the generated control information to the control apparatus 24. The controller 31 may store the control information in the memory 30.

When the communication interface 27 receives from the information processing apparatus 10 a transportation instruction, which will be described later, the controller 31, reads a transit point and the medical facility 17 from the transportation instruction. The controller 31 generates control information for controlling the vehicle 15 to travel to the medical facility 17 via the transit point.

Figure 5:
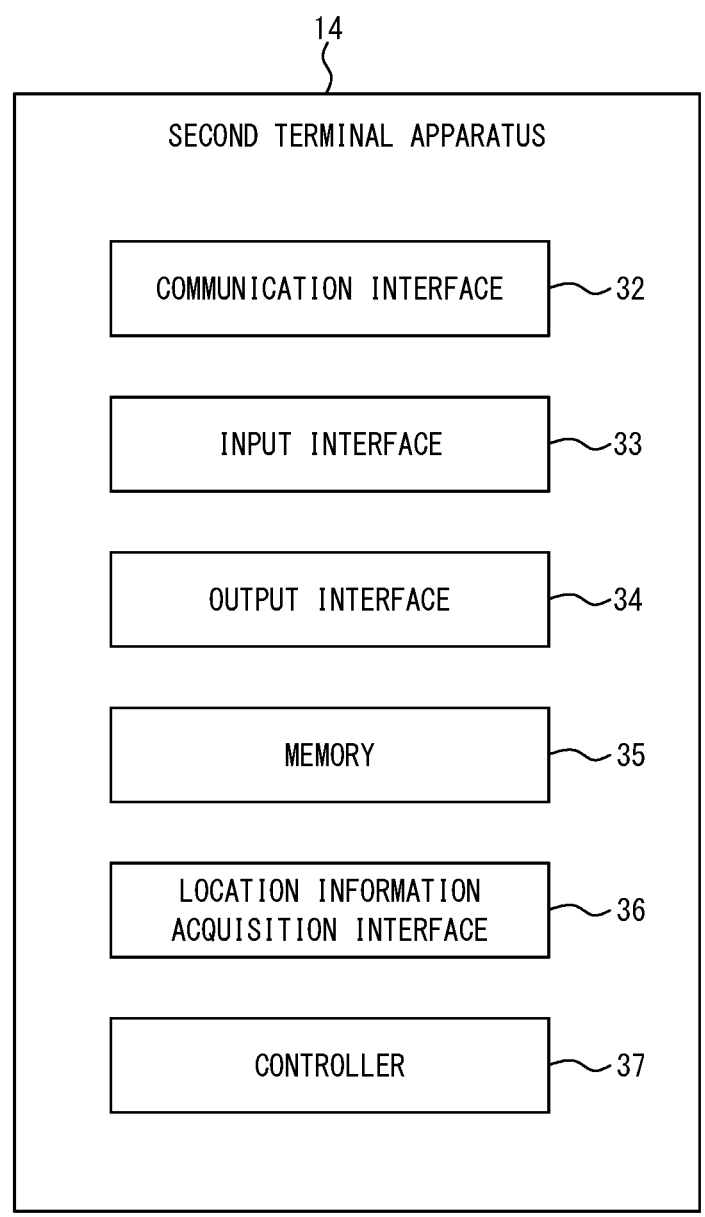
FIG. 5 is a functional block diagram schematically illustrating a configuration of a second terminal apparatus in FIG. 1.

As illustrated in FIG. 5, the second terminal apparatus 14 includes a communication interface 32, an input interface 33, an output interface 34, a memory 35, a location information acquisition interface 36, and a controller 37.

The communication interface 32 includes a communication module that establishes communication via a dedicated line. The communication interface 32 also includes a communication module that establishes connection with the network 16. For example, the communication interface may include a communication module compliant with mobile communication standards such as the 4G and 5G standards. In the present embodiment, the second terminal apparatus 14 is connected to the network 16 via the communication interface 32. The communication interface 32 sends and receives various kinds of information via the network 16.

The input interface 33 includes at least one interface that detects user inputs. For example, the input interface 33 may be, but is not limited to, physical keys, capacitive keys, a touch screen provided in combination with a display of the output interface 34, or a microphone that accepts sound input.

The output interface 34 includes at least one interface that outputs information to notify users. For example, the output interface 34 is, but not limited to, a display that outputs information as an image or a speaker that outputs information in sound.

The memory 35 may be, but is not limited to, a semiconductor memory, a magnetic memory, an optical memory, or the like. The memory 35 may function as, for example, a primary storage unit, an auxiliary storage unit, or a cache memory. The memory 35 stores any information that is used for an operation of the second terminal apparatus 14. The memory 35 may store, for example, a system program and an application program. The memory 35 may store identification information on the second terminal apparatus 14. The identification information on the second terminal apparatus 14 is information that can be used to uniquely identify the second terminal apparatus 14 in the information processing system 11. The information stored in the memory 35 may be updated using, for example, information received from the network 16 via the communication interface 32.

The location information acquisition interface 36 includes at least one receiver for a satellite navigation system. For example, the location information acquisition interface 36 may include a GPS receiver. The location information acquisition interface 36 obtains a measured value of the location of the second terminal apparatus 14 as location information for a user of the second terminal apparatus 14 and sends the measured value to the controller 37.

The controller 37 includes at least one processor. In the present embodiment, a "processor" may be, but is not limited to, a general processor or a processor specific to a particular processing operation. The controller 37 controls the entire operation of the second terminal apparatus 14.

When the input interface 33 detects a user input regarding medical service items, the controller 37 recognizes a desired medical service item in a manner similar to the controller 31 of the first terminal apparatus 13. After the controller 37 recognizes a desired medical service item, the controller 37 generates, in a manner similar to the controller 31, a medical service request including the location of the second terminal apparatus 14 and the desired medical service item. After the controller 37 completes generation of the medical service request, the controller 37 sends, in a manner similar to the controller 31, the medical service request to the information processing apparatus 10 via the communication interface 32.

When the communication interface 32 receives a notification of an available medical facility, which will be described later, for the medical service request from the information processing apparatus 10, the controller 37 causes the output interface 34 to output information for the available medical facility. When the notification includes an expected arrival time of the vehicle 15, the controller 37 may cause the output interface 34 to output the expected arrival time.

Figure 6:
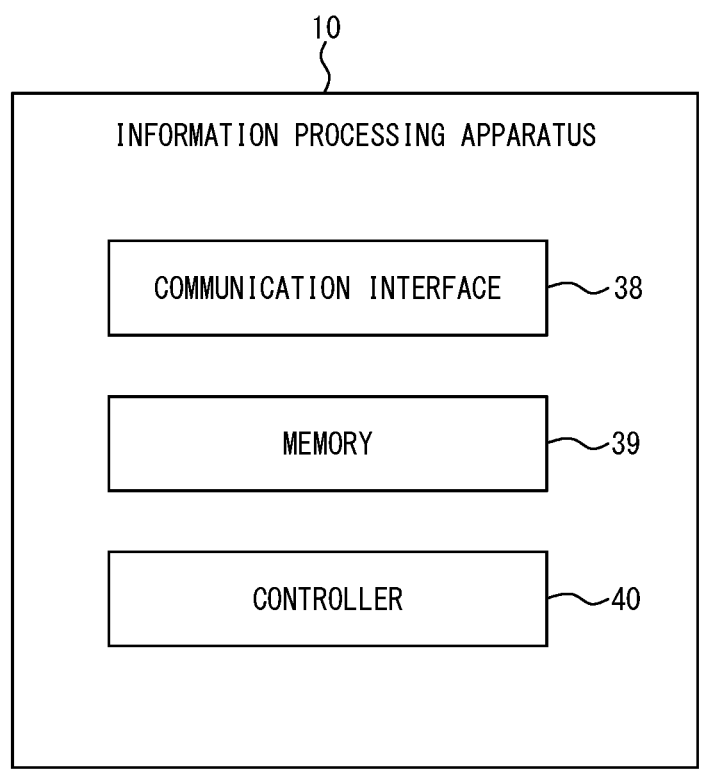
FIG. 6 is a functional block diagram schematically illustrating a configuration of the information processing apparatus in FIG. 1.

As illustrated in FIG. 6, the information processing apparatus 10 includes a communication interface 38, a memory 39, and a controller 40.

The communication interface 38 includes a communication module that establishes communication via a dedicated line. The communication interface 38 also includes a communication module that establishes connection with the network 16. For example, the communication interface may include a communication module compliant with mobile communication standards such as the 4G and 5G standards. In the present embodiment, the information processing apparatus 10 is connected to the network 16 via the communication interface 38. The communication interface 38 sends and receives various kinds of information via the network 16. The communication interface 38 can receive, from many vehicles 15, vehicle information including the location of each vehicle 15, for example.

The memory 39 may be, but is not limited to, a semiconductor memory, a magnetic memory, an optical memory, or the like. The memory 39 may function as, for example, a primary storage unit, an auxiliary storage unit, or a cache memory. The memory 39 stores any information that is used for operation of the information processing apparatus 10. The memory 39 may store the times required to provide medical services corresponding to individual medical service items. The memory 39 may store, for example, a system program and an application program.

The controller 40 includes at least one processor. In the present embodiment, a "processor" may be, but is not limited to, a general processor or a processor specific to a particular processing operation. The controller 40 controls the entire operation of the information processing apparatus 10.

When a registration request is received from the information management apparatus 12 via the communication interface 38, the controller 40 registers the information management apparatus 12. The controller 40 stores in the memory 39 an identification number of the information management apparatus 12, clinical departments, providable medical service items, and a facility location in an associated manner, which are included in the registration request, such that the controller 40 performs registration. The controller 40 may register the information management apparatuses 12 for the individual medical facilities 17.

When a scheduled vacant time period for medical services is received from the information management apparatus 12 via the communication interface 38, the controller 40 stores the scheduled vacant time period in the memory 39. The controller 40 stores the scheduled vacant time period in association with the medical facility 17 corresponding to the information management apparatus 12. The controller 40 stores the scheduled vacant time period by using for example, identification information on the information management apparatus 12 as the medical facility 17 corresponding to the information management apparatus 12. The controller 40 stores scheduled vacant time periods received from many information management apparatuses 12, and as a result, the controller 40 accumulates scheduled vacant time periods for various dates, various time slots, and various medical facilities 17.

When a medical service request is received from the first terminal apparatus 13 or the second terminal apparatus 14 via the communication interface 38, the controller 40 searches the memory 39 for the available medical facility as described above. To search for the available medical facility, the controller 40 extracts a desired medical service item and the location of a corresponding terminal apparatus that are included in the medical service request.

The controller 40 recognizes, in accordance with the medical service request, the time required to provide the medical service corresponding to the desired medical service item. In the case in which the received medical service request includes the time required to provide the medical service corresponding to the desired medical service item, the controller 40 recognize the time by extracting it from the received medical service request. Alternatively, in the case in which the received medical service request does not include the time required to provide the medical service corresponding to the desired medical service item, the controller 40 estimates the time in accordance with the desired medical service item.

The controller 40 searches the memory 39 for medical facilities 17 that can provide the medical service for the desired medical service item in a scheduled vacant time period. The medical facilities 17 that can provide the medical service for the desired medical service item in a scheduled vacant time period are the medical facilities 17 for which the desired medical service items is included in the providable medical service items and for which the time required to provide the medical service corresponding to the desired medical service item is equal to or shorter than the scheduled vacant time period.

The controller 40 further extracts, from the discovered medical facilities 17, each medical facility 17 for which there is a scheduled vacant time period after a current time. The controller 40 may limit the medical facilities 17 to be extracted to the medical facility 17 for which the facility location is included in a predetermined range from the location of the terminal apparatus. The predetermined range can be determined in any manner and, for example, the predetermined range may be a range in which residents can travel to the medical facility 17 within an allowable time and may be changed in accordance with the density of the medical facilities 17.

The controller 40 further extracts, from the extracted medical facilities 17, the medical facilities 17 that can be reached from the location of the terminal apparatus in the scheduled vacant time period. To extract the reachable medical facilities 17, the controller 40 calculates the time required to travel from the location of the terminal apparatus to the facility location of each of the extracted medical facilities 17 using the vehicle 15.

In the case in which the terminal apparatus is the first terminal apparatus 13, the controller 40 calculates a time from the location of the vehicle 15 to the facility location of the medical facility 17 as the time required for travel. In the case in which the terminal apparatus is the second terminal apparatus 14, the controller 40 searches, based on the location that is periodically received from the vehicles 15, for a vehicle 15 in an area around the location of the second terminal apparatus 14 that can travel via the location of the second terminal apparatus 14. The vehicle 15 that can travel via the location of the second terminal apparatus 14 may be, for example, a vehicle 15 that is cruising without heading toward a particular destination or a vehicle 15 that is traveling to a particular destination but can still reach the destination by an expected arrival time while traveling via the location of the second terminal apparatus 14. The controller 40 calculates, as a time required for travel from the location of the terminal apparatus by using the vehicle 15, a time from the location of the discovered vehicle 15 to the facility location of the medical facility 17 via the location of the second terminal apparatus 14.

The controller 40 extracts, as the medical facilities 17 that can be reached from the location of the terminal apparatus in the scheduled vacant time period, the medical facilities 17 to which the time required for travel by the vehicle 15 is equal to or shorter than the length of time from the current time to the start time of the scheduled vacant time period. Alternatively, the controller 40 may extract, as the medical facilities 17 that can be reached from the location of the terminal apparatus in the scheduled vacant time period, the medical facilities 17 for which the total of the time required to travel from the location of the terminal apparatus using the vehicle 15 and the time required to provide the medical service corresponding to the desired medical service item is equal to or shorter than the length of time from the current time to the end time of the scheduled vacant time period.

The controller 40 determines one particular medical facility 17 out of the extracted medical facilities 17 as an available medical facility. In the case in which a plurality of medical facilities 17 are extracted, the controller 40 may select one particular medical facility 17 in accordance with certain conditions. The certain conditions include, for example, that a time required to travel from the location of the terminal apparatus using the vehicle 15 is the shortest and that a waiting time between the time of arrival at the medical facility 17 and the start time of the scheduled vacant time period is the shortest.

The controller 40 notifies the terminal apparatus which sent the medical service request of the determined available medical facility. The controller 40 may send a notification regarding the facility location of the available medical facility. In the case in which the terminal apparatus which sent the medical service request is the first terminal apparatus 13, the controller 40 may generate a route from the location of the vehicle 15 to the facility location of the available medical facility and notify the first terminal apparatus 13 of the route. When the first terminal apparatus 13 which sent the medical service request is installed in an autonomous driving vehicle, the controller 40 may output operating instructions for travelling to the available medical facility. In the case in which the terminal apparatus which sent the medical service request is the second terminal apparatus 14, the controller 40 may output a transportation instruction to the discovered vehicle 15 that can travel via the location of the second terminal apparatus 14. The transportation instruction is an instruction for instructing the vehicle 15 to travel to a destination via a designated transit point and may include the location of the second terminal apparatus 14 as the transit point and the facility location of the available medical facility as the destination. In the case in which the terminal apparatus which sent the medical service request is the second terminal apparatus 14, the controller 40 may send a notification regarding an expected arrival time at which the discovered vehicle 15 that can travel via the location of the second terminal apparatus 14 is expected to arrive at the location of the second terminal apparatus 14.

The controller 40 sends a consultation request to the information management apparatus 12 corresponding to the medical facility 17 determined as an available medical facility. The controller 40 may include in the consultation request a time for which receiving a medical service is requested and a desired medical service item. The controller 40 may also include in the consultation request an identification number of a terminal apparatus to which an person input a medical service request and identification information for the person who made the input.

Figure 7:
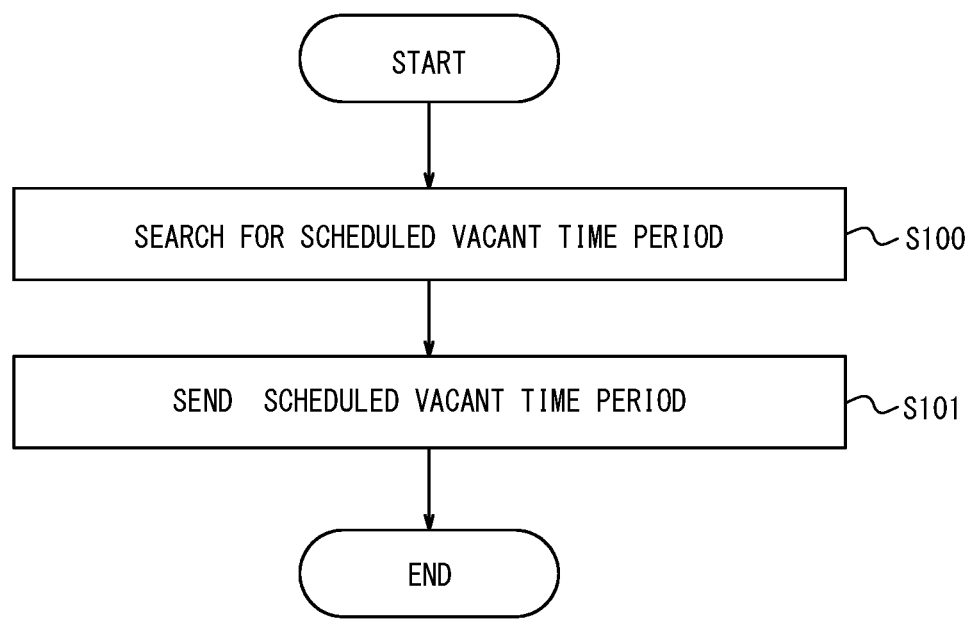
FIG. 7 is a flowchart illustrating scheduled vacant time period notification processing performed by a controller in FIG. 2.

Next, scheduled vacant time period notification processing performed by the controller 22 of the information management apparatus 12 in the present embodiment is described with reference to a flowchart in FIG. 7. The scheduled vacant time period notification processing is started when, for example, the information management apparatus 12 updates a medical service schedule.

In step S100, the controller 22 searches the updated medical service schedule for a scheduled vacant time period. After the scheduled vacant time period is detected, the process proceeds to step S101.

In step S101, the controller 22 controls the communication interface 18 to send to the information processing apparatus 10 the scheduled vacant time period discovered in step S100 in association with identification information on the information management apparatus 12. After the scheduled vacant time period is sent, the scheduled vacant time period notification processing is ended.

Figure 8:
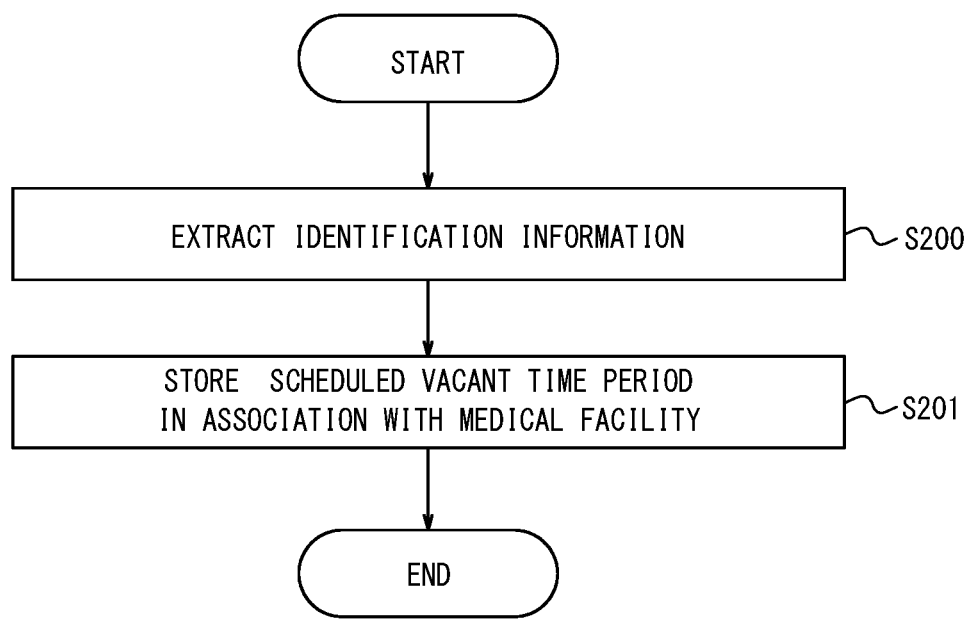
FIG. 8 is a flowchart illustrating scheduled vacant time period accumulation processing performed by a controller in FIG. 6.

Next, scheduled vacant time period accumulation processing performed by the controller 40 of the information processing apparatus 10 in the present embodiment is described with reference to a flowchart in FIG. 8. The scheduled vacant time period accumulation processing is started when, for example, the information management apparatus 12 outputs a scheduled vacant time period.

In step S200, the controller 40 extracts identification information for the information management apparatus 12 associated with the received scheduled vacant time period. After the identification information is extracted, the process proceeds to step S201.

In step S201, the controller 40 stores the scheduled vacant time period in association with the medical facility 17 corresponding to the information management apparatus 12 of the identification number extracted in step S200. After the scheduled vacant time period is stored, the scheduled vacant time period accumulation processing is ended.

Figure 9:
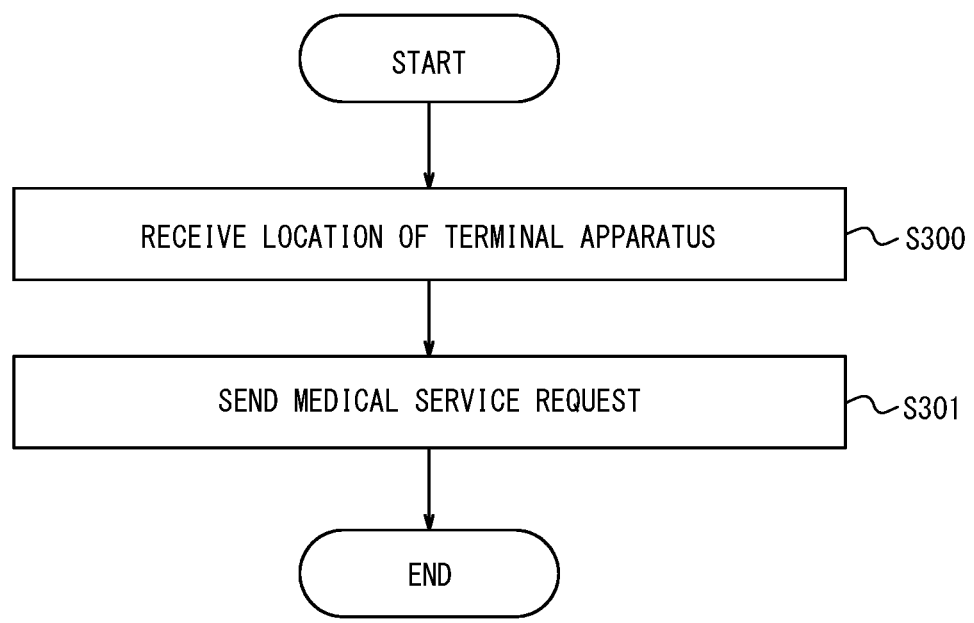
FIG. 9 is a flowchart illustrating medical service request notification processing performed by a controller in FIG. 4 or 5.

Next, medical service request notification processing performed by the controller 31 of the first terminal apparatus 13 and the controller 37 of the second terminal apparatus 14 in the present embodiment is described with reference to a flowchart in FIG. 9. The medical service request notification processing is started when, for example, the input interface 28 or 33 detects a user input of a medical service item.

In step S300, the controller 31 or 37 receives the location of the first terminal apparatus 13 or the location of the second terminal apparatus 14 from the location information acquisition apparatus 26 or the location information acquisition interface 36. After the location is received, the process proceeds to step S301.

In step S301, the controller 31 or 37 controls the communication interface 27 or 32 to send to the information processing apparatus 10 a medical service request including a desired medical service item according to a user input and the location received in step S300. After the medical service request is sent, the medical service request notification processing is ended.

Figure 10:
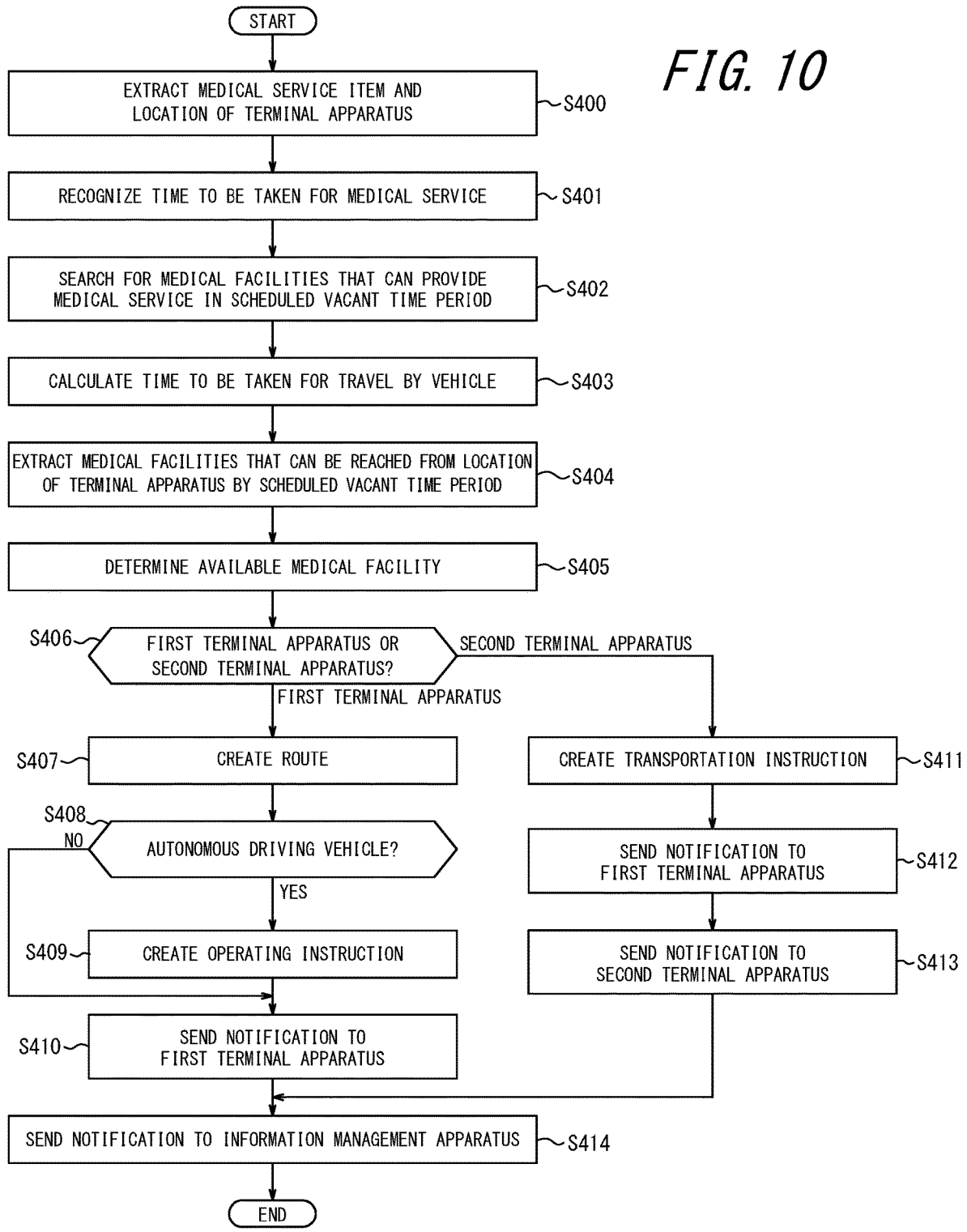
FIG. 10 is a flowchart illustrating medical facility discovery processing performed by the controller in FIG. 6.

Next, medical facility discovery processing performed by the controller 40 of the information processing apparatus 10 in the present embodiment is described with reference to a flowchart in FIG. 10. The medical facility discovery processing is started when, for example, a medical service request is received.

In step S400, the controller 40 extracts from the received medical service request a desired medical service item and a location of a terminal apparatus. After the information is extracted, the process proceeds to step S401.

In step S401, the controller 40 recognizes a time required for the medical service. After the time is recognized, the process proceeds to step S402.

In step S402, the controller 40 searches the memory 39, in accordance with the time recognized in step S401, for the medical facilities 17 that can provide the medical service corresponding to the medical service item extracted in step S400 in a scheduled vacant time period. After the medical facilities 17 are discovered, the process proceeds to step S403.

In step S403, the controller 40 calculates a time required for travel from the location of the terminal apparatus extracted in step S400 to each of the medical facilities 17 discovered in step S402 by using the vehicle 15. After the times are calculated, the process proceeds to step S404.

In step S404, the controller 40 extracts, in accordance with the times calculated in step S403, particular medical facilities 17 out of the medical facilities 17 discovered in step S402. Each of the particular medical facilities 17 can be reached from the location of the terminal apparatus in a corresponding scheduled vacant time period. After the medical facilities 17 are extracted, the process proceeds to step S405.

In step S405, the controller 40 determines, in accordance with the certain conditions, one particular medical facility 17 out of the medical facilities 17 extracted in step S404 as an available medical facility. After the one particular medical facility 17 is determined, the process proceeds to step S406.

In step S406, the controller 40 determines whether the terminal apparatus which sent the medical service request that caused the medical facility discovery processing to start, is the first terminal apparatus 13 or the second terminal apparatus 14. In the case in which the terminal apparatus is the first terminal apparatus 13, the process proceeds to step S407. In the case in which the terminal apparatus is the second terminal apparatus 14, the process proceeds to step S411.

In step S407, the controller 40 generates a route from the location of the first terminal apparatus 13 extracted in step S400 to the facility location of the available medical facility determined in step S405. After the route is generated, the process proceeds to step S408.

In step S408, the controller 40 determines whether the vehicle 15 equipped with the first terminal apparatus 13 determined in step S406 is an autonomous driving vehicle. In the case in which the first terminal apparatus 13 is an autonomous driving vehicle, the process proceeds to step S409. In the case in which the first terminal apparatus 13 is not an autonomous driving vehicle, the process proceeds to step S410.

In step S409, the controller 40 generates operating instructions for travelling from the location of the vehicle 15 to the available medical facility. After the operating instruction is generated, the process proceeds to step S410.

In step S410, the controller 40 controls the communication interface 38 to send to the first terminal apparatus 13 the available medical facility determined in step S405 together with the route generated in step S407. In the case in which an operating instruction is generated in step S409, the controller 40 controls the communication interface 38 to also send the operating instructions to the first terminal apparatus 13. After the notification of the available medical facility is sent by controlling the communication interface 38, the process proceeds to step S414.

In step S411, the controller 40 generates a transportation instruction for traveling from a location of the vehicle 15 situated in an area around the second terminal apparatus 14 via the location of the second terminal apparatus 14 to the available medical facility determined in step S405. After the transportation instruction is generated, the process proceeds to step S412.

In step S412, the controller 40 controls the communication interface 38 to send the transportation instruction generated in step S411 to the vehicle 15 that is situated in the area around the second terminal apparatus 14 and that is determined when the transportation instruction is generated in step S411. After the transportation instruction is sent by controlling the communication interface 38, the process proceeds to step S413.

In step S413, the controller 40 controls the communication interface 38 to send to the second terminal apparatus 14 the available medical facility determined in step S405 together with an expected arrival time at which the vehicle 15 to which the transportation instruction is sent in step S412 is expected to arrive at the location of the second terminal apparatus 14. After the notification of the available medical facility is sent by controlling the communication interface 38, the process proceeds to step S314.

In step S414, the controller 40 controls the communication interface 38 to send a consultation request to the information management apparatus 12 corresponding to the available medical facility determined in step S405. After the consultation request is sent by controlling the communication interface 38, the medical facility discovery processing is ended.

Figure 11:
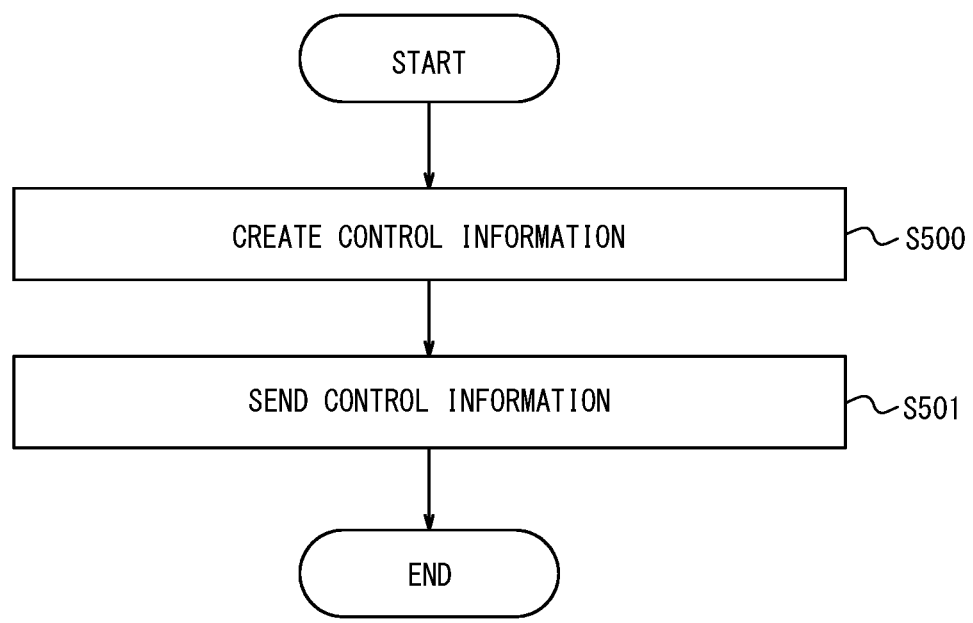
FIG. 11 is a flowchart illustrating control information generation processing performed by the controller in FIG. 4.

Next, control information generation processing performed by the controller 31 of the first terminal apparatus 13 in the present embodiment is described with reference to a flowchart in FIG. 11. The control information generation processing is started when, for example, the information processing apparatus 10 sends a notification of an available medical facility or a transportation instruction.

In step S500, the controller 31 generates control information in accordance with the received notification of an available medical facility or the received transportation instruction. After the control information is generated, the process proceeds to step S501.

In step S501, the controller 31 controls the communication interface 27 to send the control information generated in step S500 to the control apparatus 24. After the control information is sent by controlling the communication interface 27, the control information generation processing is ended.

Figure 12:
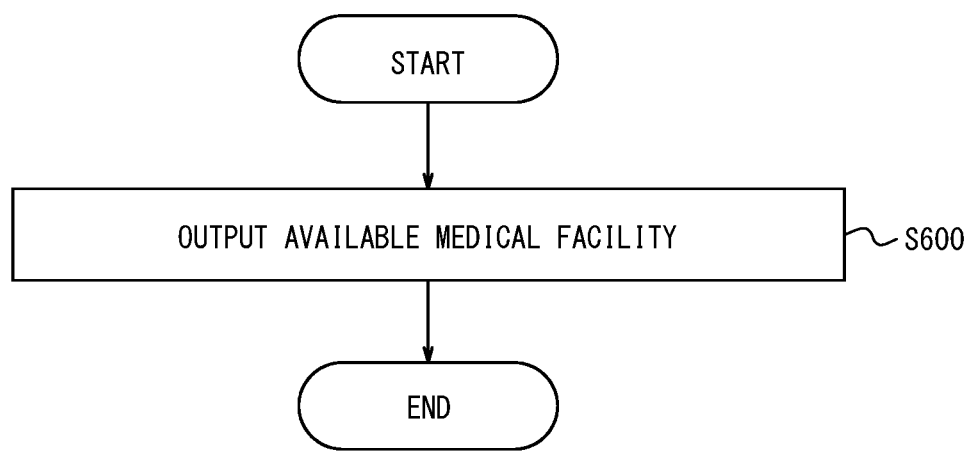
FIG. 12 is a flowchart illustrating medical facility output processing performed by the controller in FIG. 5.

Next, medical facility output processing performed by the controller 37 of the second terminal apparatus 14 in the present embodiment is described with reference to a flowchart in FIG. 12. The medical facility output processing is started when, for example, the information processing apparatus 10 sends a notification of an available medical facility.

In step S600, the controller 37 controls the output interface 34 to output the available medical facility together with an expected arrival time at which the vehicle 15 for transportation is expected to arrive at the location of the second terminal apparatus 14. After the notification of the available medical facility is sent by controlling the output interface 34, the medical facility output processing is ended.

Figure 13:
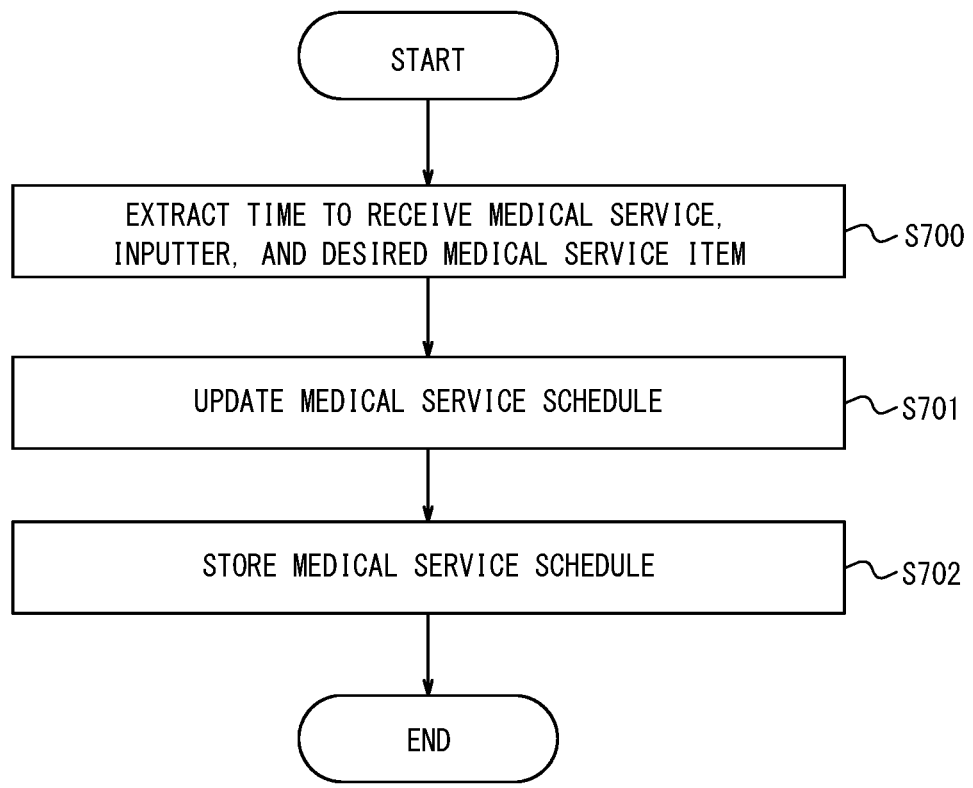
FIG. 13 is a flowchart illustrating consultation request reception processing performed by the controller in FIG. 2.

Next, consultation request reception processing performed by the controller 22 of the information management apparatus 12 in the present embodiment is described with reference to the flowchart of FIG. 13. The consultation request reception processing is started when, for example, a consultation request is received from the information processing apparatus 10.

In step S700, the controller 22 extracts, from the consultation request that caused the consultation request reception processing to start, a time for which receiving a medical service is requested, a patient who desires to receive a medical service, that is, the person who has input a medical service request to a terminal apparatus, and a desired medical service item. After the information is extracted, the process proceeds to step S701.

In step S701, the controller 22 updates a medical service schedule stored in the memory 21 to include the time for which receiving a medical service is requested, which was extracted in step S700, in a scheduled time slot. After the medical service schedule is updated, the process proceeds to step S702.

In step S702, the controller 22 stores in the memory 21 the patient and the desired medical service item extracted in step S700 in association with the time for which receiving a medical service is requested, the time being used for update in step S701. After the information is stored, the consultation request reception processing is ended.

The information processing apparatus 10 according to the present embodiment configured as described above accumulates scheduled vacant time periods in association with the medical facilities 17 and searches for a particular medical facility 17 as an available medical facility. The particular medical facility 17 is capable of providing a medical service corresponding to a medical service item included in a received medical service request in a scheduled vacant time period, and can be reached from the location of a terminal apparatus included in the medical service request in the scheduled vacant time period. The information processing apparatus 10 also sends a notification of the available medical facility to the terminal apparatus which sent the medical service request and sends a consultation request to the information management apparatus 12 corresponding to the available medical facility. With this configuration, the information processing apparatus 10 can guide the person who sent the medical service request via a terminal apparatus to the medical facility 17 that can provide the medical service at a vacant time that is after the travel time from the current location to the medical facility 17 elapses. As a result, the information processing apparatus 10 can reduce the waiting times of patients who desire to receive medical services.

Furthermore, with the configuration as described above, the information processing apparatus 10 sends to the information management apparatus 12 only a particular medical service item as a consultation request. A medical service corresponding to the particular medical service item can be completed within a scheduled vacant time period. In usual cases, if a medical facility not using the information processing system 11 determines medical service slots excluding scheduled times with appointments as time slots for which priority is given to patients who desires to receive medical services on the same day, patients do not always attend the medical facility during the determined medical service slots. In contrast, the information processing apparatus 10 having the configuration described above can reduce the possibility that no patient attends during a scheduled vacant time period, whereby an opportunity to provide medical services is lost. This may encourage many medical facilities to introduce the information processing system 11. If the medical facilities 17 introducing the information processing system 11 increase, the possibility that the information processing apparatus 10 is able to secure scheduled vacant time periods is strengthened. As a result, the information processing apparatus 10 can further increase the potential for guiding patients who desire to receive medical services to available medical facilities.

Moreover, the information processing apparatus 10 sends to the information management apparatus 12 only a particular medical service item as a consultation request. A medical service corresponding to the particular medical service item can be completed within a scheduled vacant time period.

This can reduce the likelihood of delaying a medical service of an appointment that is received by the medical facility 17 and that is after a fixed time slot for which priority is given to a consultation request submitted from a terminal apparatus. Thus, the information processing apparatus 10 may encourage the medical facility 17 to set a fixed time slot. This increases the potential for securing scheduled vacant time periods. As a result, the information processing apparatus 10 can further increase the potential for guiding patients who desire to receive medical services to available medical facilities.

Further, in the case in which the terminal apparatus sending a medical service request is the second terminal apparatus 14, the information processing apparatus 10 searches for a vehicle 15 situated in an area around the location of the second terminal apparatus 14 and searches for the medical facility 17 that can be reached from the location of the vehicle 15 via the location of the second terminal apparatus 14 in a scheduled vacant time period. Moreover, the information processing apparatus 10 notifies the vehicle 15 of the location of the second terminal apparatus 14 and an available medical facility. With this configuration, the information processing apparatus 10 can send to the current location of a person who inputs a medical service request the vehicle 15 that provides a ride to the available medical facility for the person. Consequently, the information processing apparatus 10 can improves the convenience for the person who inputs the medical service request.

While the present disclosure has been described with reference to the accompanying drawings and the examples, it should be understood that various changes and modifications based on the present disclosure may be easily made by those skilled in the art. These changes and modifications are therefore embraced in the scope of the present disclosure. For example, the functions and the like included in the constituents and steps may be rearranged in a logically consistent manner, and a plurality of constituents or steps may be combined together or divided.

Furthermore, for example, part of the processing operation performed by the information processing apparatus 10 in the embodiment described above may be carried out by at least any of the information management apparatus 12, the first terminal apparatus 13, and the second terminal apparatus 14. Part of the processing operation performed by at least any of the information management apparatus 12, the first terminal apparatus 13, and the second terminal apparatus 14 may be carried out by the information processing apparatus 10.

Furthermore, for example, a general electronic device such as a smartphone or a computer may be configured to function as the information processing apparatus 10, the information management apparatus 12, the first terminal apparatus 13, or the second terminal apparatus 14 according to the embodiment described above. Specifically, a memory of an electronic device stores a program in which details of processing for implementing the functions of, for example, the information processing apparatus 10 according to the embodiment are written, and a processor of the electronic device reads and runs the program. Thus, the disclosure according to the present embodiment may be implemented as a program that can be run by a processor. The program may be downloaded via the network 16, or the program may be stored in a non-transitory recording/storage medium readable by electronic devices and the program may be read from the medium by an electronic device.

The invention claimed is:

1. An information processing apparatus comprising:
   a memory configured to store providable medical service items and a facility location in association with each of medical facilities;
   a communication interface configured to communicate with a terminal apparatus and with information management apparatuses that correspond to respective ones of the medical facilities; and
   a controller configured to:
     upon receiving, from a first information management apparatus via the communication interface, information on a scheduled vacant time period that is a time slot obtained by excluding scheduled time slots from a schedule of medical services provided at a medical facility corresponding to the first information management apparatus, store the scheduled vacant time period in the memory in association with the medical facility corresponding to the first information management apparatus;
     upon receiving, from the terminal apparatus via the communication interface, a medical service request including a desired medical service item and a location of the terminal apparatus, determine whether the terminal apparatus is a first terminal apparatus installed in a vehicle or a second terminal apparatus not installed in a vehicle;
     upon determining that the terminal apparatus is the first terminal apparatus, search the memory for a particular medical facility as an available medical facility, a providable medical service item stored in the memory in association with the particular medical facility being coincident with the desired medical service item included in the medical service request and a time required for travel by vehicle from the location of the terminal apparatus included in the medical service request to a facility location stored in the memory in association with the particular medical facility being less than a remaining time until an end time of a scheduled vacant time period stored in the memory in association with the particular medical facility;
     upon determining that the terminal apparatus is the second terminal apparatus, detect a vehicle situated in an area around the location of the terminal apparatus included in the medical service request, and search the memory for a particular medical facility as an available medical facility, a providable medical service item stored in the memory in association with the particular medical facility being coincident with the desired medical service item included in the medical service request and a time required for travel by vehicle from a location of the detected vehicle via the location of the terminal apparatus included in the medical service request to a facility location stored in the memory in association with the particular medical facility being less than a remaining time until an end time of a scheduled vacant time period stored in the memory in association with the particular medical facility;

send, via the communication interface, a notification of the available medical facility to the terminal apparatus; and send, via the communication interface, a consultation request to request a medical service in a scheduled vacant time period stored in the memory in association with the available medical facility, to a second information management apparatus corresponding to the available medical facility.

2. The information processing apparatus according to claim 1, wherein upon determining that the terminal apparatus is the first terminal apparatus, the controller is configured to generate a route from a location of the vehicle in which the first terminal apparatus is installed to a facility location stored in the memory in association with the available medical facility and send the route to the first terminal apparatus.

3. The information processing apparatus according to claim 2, wherein when the first terminal apparatus is installed in an autonomous driving vehicle, the controller is configured to send to the first terminal apparatus an operating instruction for reaching the available medical facility.

4. The information processing apparatus according to claim 1, wherein the controller is configured to estimate a medical service time required to provide a medical service corresponding to the desired medical service item included in the medical service request and search the memory for the available medical facility by determining whether a sum of the time required for travel by vehicle and the medical service time is equal to or less than the remaining time.

5. An information processing system comprising:
the information processing apparatus according to claim 1;
the terminal apparatus; and
the information management apparatuses, wherein
the first terminal apparatus is configured to send to the information processing apparatus, as the location of the terminal apparatus included in the medical service request, a measured value obtained by a satellite navigation system receiver installed in the vehicle in which the first terminal apparatus is installed, and
the second terminal apparatus is configured to send to the information processing apparatus, as the location of the terminal apparatus included in the medical service request, a measured value obtained by a satellite navigation system receiver installed in the second terminal apparatus.

6. The information processing system according to claim 5, wherein upon determining that the terminal apparatus is the first terminal apparatus, the controller is configured to generate a route from a location of the vehicle in which the first terminal apparatus is installed to a facility location stored in the memory in association with the available medical facility and send the route to the first terminal apparatus.

7. The information processing system according to claim 6, wherein when the first terminal apparatus is installed in an autonomous driving vehicle, the controller is configured to send to the first terminal apparatus an operating instruction for reaching the available medical facility.

8. The information processing system according to claim 5, wherein the controller is configured to estimate a medical service time required to provide a medical service corresponding to the desired medical service item included in the medical service request and search the memory for the available medical facility by determining whether a sum of the time required for travel by the vehicle and the medical service time is equal to or less than the remaining time.

9. The information processing system according to claim 5, wherein the controller is configured to, upon extracting a plurality of medical facilities as the available medical facility, select one medical facility as the available medical facility, a waiting time between time of arrival at the one medical facility and a start time of the scheduled vacant time period stored in the memory in association with the one medical facility is shortest among the plurality of medical facilities.

10. The information processing apparatus according to claim 1, wherein the controller is configured to, upon extracting a plurality of medical facilities as the available medical facility, select one medical facility as the available medical facility, a waiting time between time of arrival at the one medical facility and a start time of the scheduled vacant time period stored in the memory in association with the one medical facility is shortest among the plurality of medical facilities.

11. A non-transitory computer-readable storage medium storing a program which, when executed by an information processing apparatus, causes the information processing apparatus to execute a process, the process comprising:

store in memory providable medical service items and a facility location in association with each of medical facilities;

communicate with a terminal apparatus and with information management apparatuses that correspond to respective ones of the medical facilities;

upon receiving, from a first information management apparatus information on a scheduled vacant time period that is a time slot obtained by excluding scheduled time slots from a schedule of medical services provided at a medical facility corresponding to the first information management apparatus, store the scheduled vacant time period in the memory in association with the medical facility corresponding to the first information management apparatus;

upon receiving, from the terminal apparatus a medical service request including a desired medical service item and a location of the terminal apparatus, determine whether the terminal apparatus is a first terminal apparatus installed in a vehicle or a second terminal apparatus not installed in a vehicle;

upon determining that the terminal apparatus is the first terminal apparatus, search the memory for a particular medical facility as an available medical facility, a providable medical service item stored in the memory in association with the particular medical facility being coincident with the desired medical service item included in the medical service request and a time required for travel by vehicle from the location of the terminal apparatus included in the medical service request to a facility location stored in the memory in association with the particular medical facility being less than a remaining time until an end time of a scheduled vacant time period stored in the memory in association with the particular medical facility;

upon determining that the terminal apparatus is the second terminal apparatus, detect a vehicle situated in an area around the location of the terminal apparatus included in the medical service request, and search the memory for a particular medical facility as an available medical facility, a providable medical service item stored in the memory in association with the particular medical facility being coincident with the desired medical service item included in the medical service request and a time required for travel by vehicle from a location of the detected vehicle via the location of the terminal apparatus included in the medical service request to a facility location stored in the memory in association with the particular medical facility being less than a remaining time until an end time of a scheduled vacant time period stored in the memory in association with the particular medical facility;

send a notification of the available medical facility to the terminal apparatus; and send a consultation request to request a medical service in a scheduled vacant time period stored in the memory in association with the available medical facility, to a second information management apparatus corresponding to the available medical facility.

12. The non-transitory computer-readable storage medium storing the program according to claim 11, the process further comprising:
upon determining that the terminal apparatus is the first terminal apparatus, generating a route from a location of the vehicle in which the first terminal apparatus is installed to a facility location stored in the memory in association with the available medical facility; and
sending the route to the first terminal apparatus.

13. The non-transitory computer-readable storage medium storing the program according to claim 12, the process further comprising:
when the first terminal apparatus is installed in an autonomous driving vehicle, sending to the first terminal apparatus an operating instruction for reaching the available medical facility.

14. The non-transitory computer-readable storage medium storing the program according to claim 11, the process further comprising:
estimating a medical service time required to provide the medical service corresponding to the desired medical service item included in the medical service request; and
searching for the available medical facility by determining whether a sum of the time required for travel by vehicle and the medical service time is equal to or less than the remaining time.

15. The non-transitory computer-readable storage medium storing the program according to claim 11, wherein
upon extracting a plurality of medical facilities as the available medical facility, select one medical facility as the available medical facility, a waiting time between time of arrival at the one medical facility and a start time of the scheduled vacant time period stored in the memory in association with the one medical facility is shortest among the plurality of medical facilities.

16. An information processing method implemented by an information processing apparatus, comprising:
receiving, from a first information management apparatus, information on a scheduled vacant time period that is a time slot obtained by excluding scheduled time slots from a schedule of medical services provided at a medical facility corresponding to the first information management apparatus,
accumulating the scheduled vacant time period in association with the medical facility corresponding to the first information management apparatus;
receiving, from a terminal apparatus, a medical service request including a desired medical service item and a location of the terminal apparatus, determine whether the terminal apparatus is a first terminal apparatus installed in a vehicle or a second terminal apparatus not installed in a vehicle;
upon determining that the terminal apparatus is the first terminal apparatus, search the accumulated information for a particular medical facility as an available medical facility, a providable medical service item stored in association with the particular medical facility being coincident with the desired medical service item included in the medical service request and a time required for travel by vehicle from the location of the terminal apparatus included in the medical service request to a facility location in association with the particular medical facility being less than a remaining time until an end time of a scheduled vacant time period in association with the particular medical facility;
upon determining that the terminal apparatus is the second terminal apparatus, detect a vehicle situated in an area around the location of the terminal apparatus included in the medical service request, and search the accumulated information for a particular medical facility as an available medical facility, a providable medical service item stored in association with the particular medical facility being coincident with the desired medical service item included in the medical service request and a time required for travel by vehicle from a location of the detected vehicle via the location of the terminal apparatus included in the medical service request to a facility location stored in association with the particular medical facility being less than a remaining time until an end time of a scheduled vacant time period in association with the particular medical facility;
send a notification of the available medical facility to the terminal apparatus; and
send a consultation request to request a medical service in a scheduled vacant time period in association with the available medical facility, to a second information management apparatus corresponding to the available medical facility.

17. The information processing method according to claim 16, further comprising:
upon determining that the terminal apparatus is the first terminal apparatus, generating a route from a location of the vehicle in which the first terminal apparatus is installed to a facility location stored in the memory in association with the available medical facility; and
sending the route to the first terminal apparatus.

18. The information processing method according to claim 17, further comprising:

when the first terminal apparatus is installed in an autonomous driving vehicle, sending to the first terminal apparatus an operating instruction for reaching the available medical facility.

19. The information processing method according to claim 16, further comprising:
    estimating a medical service time required to provide a medical service corresponding to the desired medical service item included in the medical service request; and
    searching for the available medical facility by determining whether a sum of the time required to travel by vehicle and the medical service time is equal to or less than the remaining time period.

20. The information processing method according to claim 16, wherein
    upon extracting a plurality of medical facilities as the available medical facility, select one medical facility as the available medical facility, a waiting time between time of arrival at the one medical facility and a start time of the scheduled vacant time period stored in the memory in association with the one medical facility is shortest among the plurality of medical facilities.

\* \* \* \* \*